(12) United States Patent
Nelson et al.

(10) Patent No.: US 6,878,126 B2
(45) Date of Patent: *Apr. 12, 2005

(54) CONTOURED KNEE BRACE FRAME

(75) Inventors: Kim Alex Nelson, Salt Lake City, UT (US); Lonnie E. Paulos, Salt Lake City, UT (US)

(73) Assignee: dj Orthopedics, LLC, Vista, CA (US)

( * ) Notice: Subject to any disclaimer, the term of this patent is extended or adjusted under 35 U.S.C. 154(b) by 24 days.

This patent is subject to a terminal disclaimer.

(21) Appl. No.: 10/669,136

(22) Filed: Sep. 23, 2003

(65) Prior Publication Data

US 2004/0133139 A1 Jul. 8, 2004
US 2004/0204667 A2 Jul. 8, 2004

Related U.S. Application Data

(63) Continuation of application No. 09/945,115, filed on Aug. 31, 2001, now Pat. No. 6,623,439.

(51) Int. Cl.[7] .................................................. A61F 5/00
(52) U.S. Cl. .............................. 602/26; 602/16; 128/882
(58) Field of Search .............................. 602/5, 16, 23, 602/26, 27; 128/882; 623/39; 2/22, 24; 482/114, 115; 601/34

(56) References Cited

U.S. PATENT DOCUMENTS

| | | | |
|---|---|---|---|
| 431,797 A | 7/1890 | Blattmach'r |
| 559,835 A | 5/1896 | Allen |
| 932,177 A | 8/1909 | Roth |
| 2,144,641 A | 1/1938 | Snyder |
| 2,195,024 A | 3/1940 | Bullock |
| 3,055,359 A | 9/1962 | Palmer |
| 3,350,719 A | 11/1967 | McClure, Jr. |
| 3,528,412 A | 9/1970 | McDavid |
| 3,958,569 A | 5/1976 | Vosburgh |
| 4,136,404 A | 1/1979 | Lange |
| 4,183,099 A | 1/1980 | Lacey |
| 4,220,148 A | 9/1980 | Lehneis |
| 4,241,730 A | 12/1980 | Helfet |
| RE30,501 E | 2/1981 | Almeida |
| 4,256,097 A | 3/1981 | Willis |
| 4,271,831 A | 6/1981 | Deibert |
| 4,275,716 A | 6/1981 | Scott, Jr. |
| 4,337,764 A | 7/1982 | Lerman |
| 4,340,041 A | 7/1982 | Frank |
| 4,353,361 A | 10/1982 | Foster |
| 4,361,142 A | 11/1982 | Lewis et al. |
| 4,372,298 A | 2/1983 | Lerman |

(Continued)

FOREIGN PATENT DOCUMENTS

| | | |
|---|---|---|
| DE | 2239382 | 2/1974 |
| EP | 0512 666 A1 | 11/1992 |
| GB | 2136294 | 9/1984 |
| WO | WO 01/89434 A1 | 11/2001 |

OTHER PUBLICATIONS

Advertisement: "*The GII Unloader©*: A New Pain Relief Option for Osteoarthritis Patients," Generation II USA Inc. (after 1993).

(Continued)

*Primary Examiner*—Danton DeMille
*Assistant Examiner*—Quang D. Thanh
(74) *Attorney, Agent, or Firm*—Knobbe, Martens, Olson & Bear, LLP

(57) ABSTRACT

The present invention provides an improved knee brace that is configured to improve comfort to the user and reduce interference with the natural motion of the user's leg. The knee brace has rigid upper and lower frames that are connected together by polycentric hinges. The rigid upper frame is contoured such that no rigid structure is located along the medial superior region of the thigh. The rigid upper and lower frames are secured to the leg using a plurality of straps.

12 Claims, 4 Drawing Sheets

U.S. PATENT DOCUMENTS

| | | |
|---|---|---|
| 4,379,463 A | 4/1983 | Meier et al. |
| 4,381,768 A | 5/1983 | Erichsen et al. |
| 4,388,920 A | 6/1983 | Hajost et al. |
| 4,433,679 A | 2/1984 | Mauldin et al. |
| 4,493,316 A | 1/1985 | Reed et al. |
| 4,494,534 A | 1/1985 | Hutson |
| 4,506,661 A | 3/1985 | Foster |
| 4,531,515 A | 7/1985 | Rolfes |
| 4,556,053 A | 12/1985 | Irons |
| 4,572,170 A | 2/1986 | Cronk et al. |
| 4,607,628 A | 8/1986 | Dashefsky |
| 4,624,247 A | 11/1986 | Ford |
| 4,632,098 A | 12/1986 | Grundei et al. |
| 4,633,867 A | 1/1987 | Kausek et al. |
| 4,686,969 A | 8/1987 | Scott |
| 4,697,583 A | 10/1987 | Mason et al. |
| 4,768,500 A | 9/1988 | Mason et al. |
| 4,796,610 A | 1/1989 | Cromartie |
| 4,817,588 A | 4/1989 | Bledsoe |
| 4,854,308 A | 8/1989 | Drillio |
| 4,872,448 A | 10/1989 | Johnson, Jr. |
| 4,887,590 A | 12/1989 | Logue et al. |
| 4,940,044 A | 7/1990 | Castillo |
| 4,940,045 A | 7/1990 | Cromartie |
| 4,941,462 A | 7/1990 | Lindberg |
| 4,955,369 A | 9/1990 | Bledsoe et al. |
| 4,986,264 A | 1/1991 | Miller |
| 5,002,045 A | 3/1991 | Spademan |
| 5,022,391 A | 6/1991 | Weidenburner |
| 5,025,782 A | 6/1991 | Salerno |
| 5,042,464 A | 8/1991 | Skwor et al. |
| 5,086,761 A | 2/1992 | Ingram |
| 5,131,385 A | 7/1992 | Kuehnegger et al. |
| 5,135,469 A | 8/1992 | Castillo |
| 5,277,697 A | 1/1994 | France et al. |
| 5,277,698 A | 1/1994 | Taylor |
| 5,288,287 A | 2/1994 | Castillo et al. |
| 5,292,303 A | 3/1994 | Bastyr et al. |
| 5,360,394 A | 11/1994 | Christensen |
| 5,383,845 A | 1/1995 | Nebolon |
| 5,387,185 A | 2/1995 | Johnson, Jr. et al. |
| 5,400,806 A | 3/1995 | Taylor |
| 5,409,449 A | 4/1995 | Nebolon |
| 5,415,625 A | 5/1995 | Cassford et al. |
| 5,433,699 A | 7/1995 | Smith, III |
| 5,458,565 A | 10/1995 | Tillinghast, III et al. |
| 5,527,268 A | 6/1996 | Gildersleeve et al. |
| D372,983 S | 8/1996 | Nebolon |
| 5,558,627 A | 9/1996 | Singer et al. |
| 5,743,865 A | 4/1998 | Townsend |
| 5,782,780 A | 7/1998 | Mason et al. |
| 5,792,086 A | 8/1998 | Bleau et al. |
| 5,797,864 A | 8/1998 | Taylor |
| 5,807,294 A | 9/1998 | Cawley et al. |
| 5,814,000 A | 9/1998 | Kilbey |
| 5,873,848 A | 2/1999 | Fulkerson |
| 5,891,071 A | 4/1999 | Stearns et al. |
| 6,623,439 B1 * | 9/2003 | Nelson et al. ............... 602/26 |

OTHER PUBLICATIONS

Article: "Specter ROM & P–ROM Braces," FLA Orthopedics, Inc., Rehab and Therapy Products Review, Sep./Oct. 1998.

Advertisement: FlexTech, "T.K.R. Brace, Recurvatum, Trigger–Lock, and B.K. Brace," 1998 AOPA Show.

Advertisement: Bledsoe Thrusher Knee Brace (after 1993).

International Search Report; application No. PCT/US02/28083; filed Aug. 30, 2002.

* cited by examiner

CONTOURED KNEE BRACE FRAME

RELATED APPLICATION

The present application is a continuation application of U.S. application Ser. No. 09/945,115, filed Aug. 31, 2001, now U.S. Pat. No. 6,623,439, the entirety of which is herein incorporated by reference.

BACKGROUND OF THE INVENTION

1. Field of the Invention

The present invention relates to knee braces. More particularly, the invention relates to a contoured knee brace frame adapted for improved comfort and performance.

2. Description of the Related Art

The human knee generally comprises an articulating joint between the thigh and calf muscle groups that supports the weight of the body while a person is standing, walking or running. The joint is primarily held together by four small but strong ligaments, namely, the anterior and posterior cruciate ligaments and the medial and lateral collateral ligaments. The knee is a relatively weak joint and therefore knee injuries arising out of cartilage damage, ligament strain, and other causes are relatively commonplace. Knee injuries are particularly likely to occur during physical activities in which the knees are subjected to significant lateral loads. Among the numerous physical activities in which knee injuries can occur, skiing and motorcycle racing have proven to be particularly hazardous.

To help prevent knee injuries, various types of "preventive" knee braces have been proposed to help support and reinforce the knee. Preventive knee braces generally include upper and lower rigid members that are connected together by a pair of mechanical hinges. The upper and lower rigid members are typically made of a hard plastic and are secured to the leg by a number of straps.

Although various types of preventive knee braces have been proposed, many of these knee braces are uncomfortable to wear during certain physical activities because the rigid upper member of the knee brace presses against the medial superior thigh region of the user's leg. This discomfort detracts from the enjoyment of the activity and can adversely affect the user's performance. Particular examples of activities wherein the upper rigid member may produce undesirable pressure along the medial superior thigh include motorcycle racing and horseback riding.

Furthermore, when worn on both legs, it has been found that many of the proposed knee braces are configured such that the upper rigid members of the left and right knee braces impact each other along the medial superior thigh region during certain activities. This is a significant shortcoming since contact between knee braces adversely affects the natural motion of the legs and also produces undesirable noise. Skiing is an activity in which this problem is particularly troublesome. The bumps and vibrations experienced while skiing cause the knee braces to impact each other on a continual basis. This problem is especially apparent while skiing at high speeds, such as during downhill racing, and can significantly impact the skier's performance. Worse yet, in some cases, it has been found that the knee brace frames can actually catch on each other, thereby causing the skier to fall and possibly resulting in a serious injury.

In recent years, various attempts have been made to provide a knee brace with a reduced profile along the medial superior thigh region to help minimize these problems. However, none of the existing knee braces has been sufficient to achieve this goal while still providing adequate support and effectively preventing injuries to the four primary knee ligaments. Many of the proposed knee braces are configured with a relatively large clearance between the rigid frame and the leg around the knee joint. Because the rigid frame does not fit snugly onto the leg, the knee joint can move or bend in undesirable directions and can therefore damage the ligaments. Furthermore, the proposed knee braces have a relatively high profile and are therefore much more likely to catch or snag on a foreign object during physical activity.

Therefore, a need exists for an improved knee brace frame that is configured to reduce or eliminate the above shortcomings while still maintaining excellent stability and support of the knee joint. It is desirable that such a knee brace frame has no rigid structure along the medial superior thigh and is therefore comfortable to wear. It is also desirable that such a knee brace frame is configured such that it will not impact a knee brace worn on the opposite leg. It is also desirable that such a knee brace frame is constructed with a low profile such that it will not catch on a foreign object. It is also desirable that such a knee brace frame fits snugly onto the leg and has a very small clearance between the rigid frame and the leg to firmly control the motion of the knee joint. It is also desirable that such a knee brace frame is constructed of a durable material that is resistant to corrosion. Finally, to be practical, it is also desirable that such a knee brace frame is relatively inexpensive to manufacture and is aesthetically appealing. The present invention addresses these needs.

SUMMARY OF THE INVENTION

The preferred embodiments of the present invention provide a new and improved knee brace that provides excellent support to the knee joint while being very comfortable to wear. In a significant feature of the present invention, the knee brace frame is contoured such that no rigid structure is located along the medial superior region of the thigh. As a result, the preferred embodiments of the present invention do not produce pressure along the inner thigh and do not interfere with an opposing knee brace or the natural motion of the leg.

The knee brace frame is generally characterized by upper and lower rigid members that are connected together by polycentric hinges located along the axis of the knee. In a preferred embodiment, the upper rigid member is formed as a single continuous piece that circumvents the medial superior thigh, yet can still be firmly attached to the thigh to provide excellent support and stability of the knee joint.

All the preferred embodiments of the present invention have tremendous structural integrity and can withstand the application of large forces over long periods of time. In addition, the preferred embodiments are easy to assemble and use many parts that are common to knee brace frames that are currently in existence.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
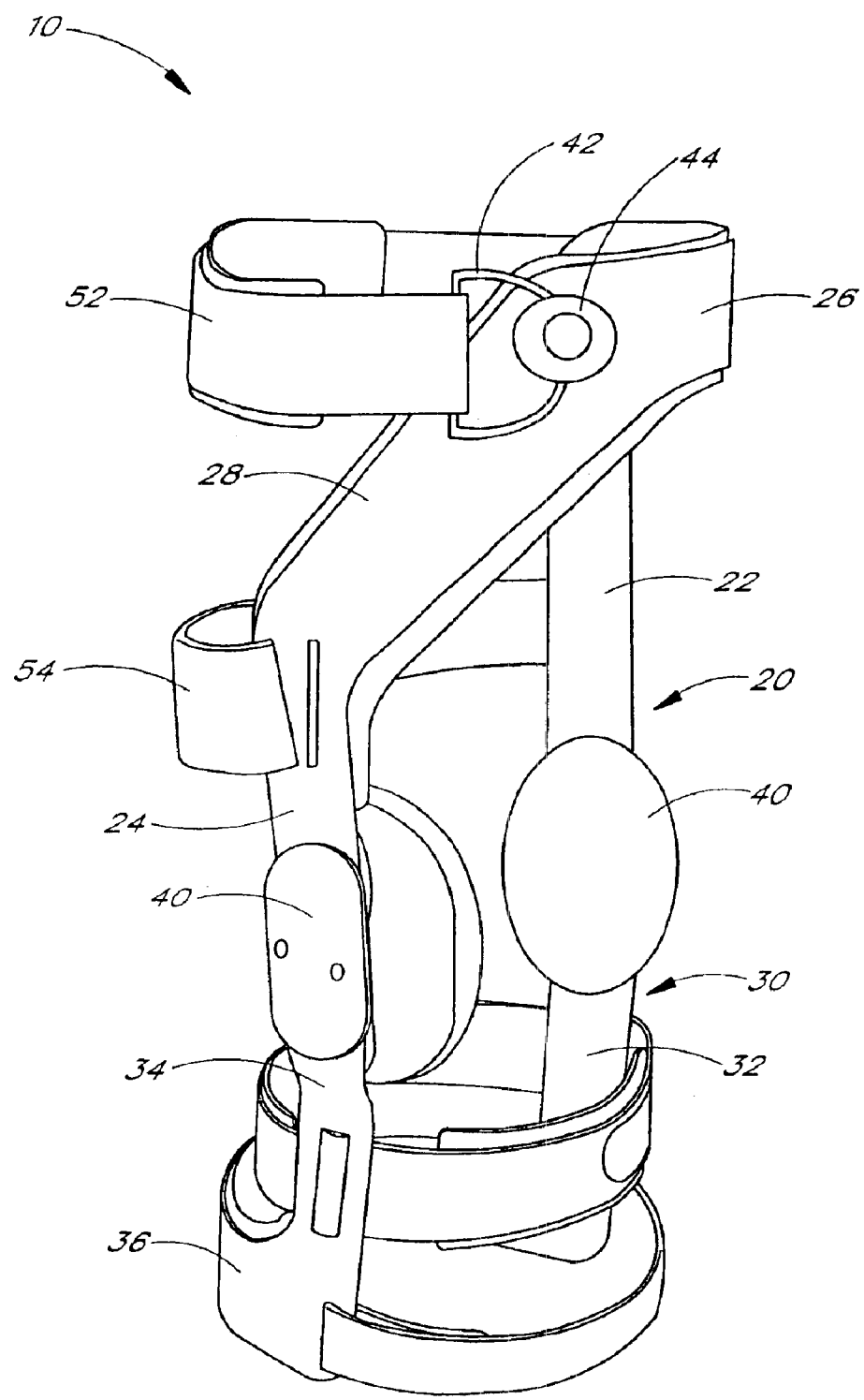
FIG. 1 is a perspective view of a preferred embodiment of a knee brace according to the present invention.

FIG. 1 illustrates a preferred embodiment of a knee brace 10 according to the present invention. The illustrated knee brace 10 is intended for use on the left leg and includes an upper rigid member 20, a lower rigid member 30, and polycentric hinges 40 located along the axis of the knee joint. The knee brace 10 maintains the thigh and calf in proper alignment and thereby prevents injuries caused by lateral knee joint displacement. The polycentric hinges 40 are configured with a limited range of rotation to prevent hyperextension of the lower leg. The knee brace 10 is also provided with a plurality of straps for securing the upper 20 and lower 30 members to the respective thigh and calf portions of the leg. The illustrated knee brace 10 is preferably used to prevent injuries to the knee joint; however, the knee brace may also be used to support the knee joint during rehabilitation after an injury.

In an important feature of the present invention, the rigid upper member 20 of the knee brace 10 is constructed such that no rigid structure is located along the medial superior thigh region of the leg. As a result, the knee brace 10 is very comfortable to wear and does not interfere with the natural motion of the leg. At the same time, the improved structure is shaped with a low profile that significantly reduces the likelihood that the knee brace will not catch or snag on a foreign object.

The illustrated embodiment of the present invention is constructed such that the upper rigid member 20 is formed as a single continuous piece having four primary segments: an upper lateral segment 22, an upper medial segment 24, an upper curved segment 26, and an angled segment 28. The rigid lower member 30 is formed as a single continuous piece having three primary segments: a lower lateral segment 32, a lower medial segment 34 and a lower curved segment 36. It will be appreciated that the knee brace frame could also be constructed of multiple rigid segments joined together to form upper and lower rigid members.

As illustrated in the preferred embodiment of FIG. 1, the upper medial segment 24 is significantly shorter in length than the upper lateral segment 22. Preferably, the upper medial segment 24 is about 30% to 70% shorter than the upper lateral segment 22. Most preferably, the upper medial segment 24 is about 50% shorter than the upper lateral segment 22. Because the upper medial segment 24 has a shortened length, the upper rigid member 20 of the knee brace 10 does not extend up into the medial superior (i.e. inner upper) portion of the thigh.

Figure 2:
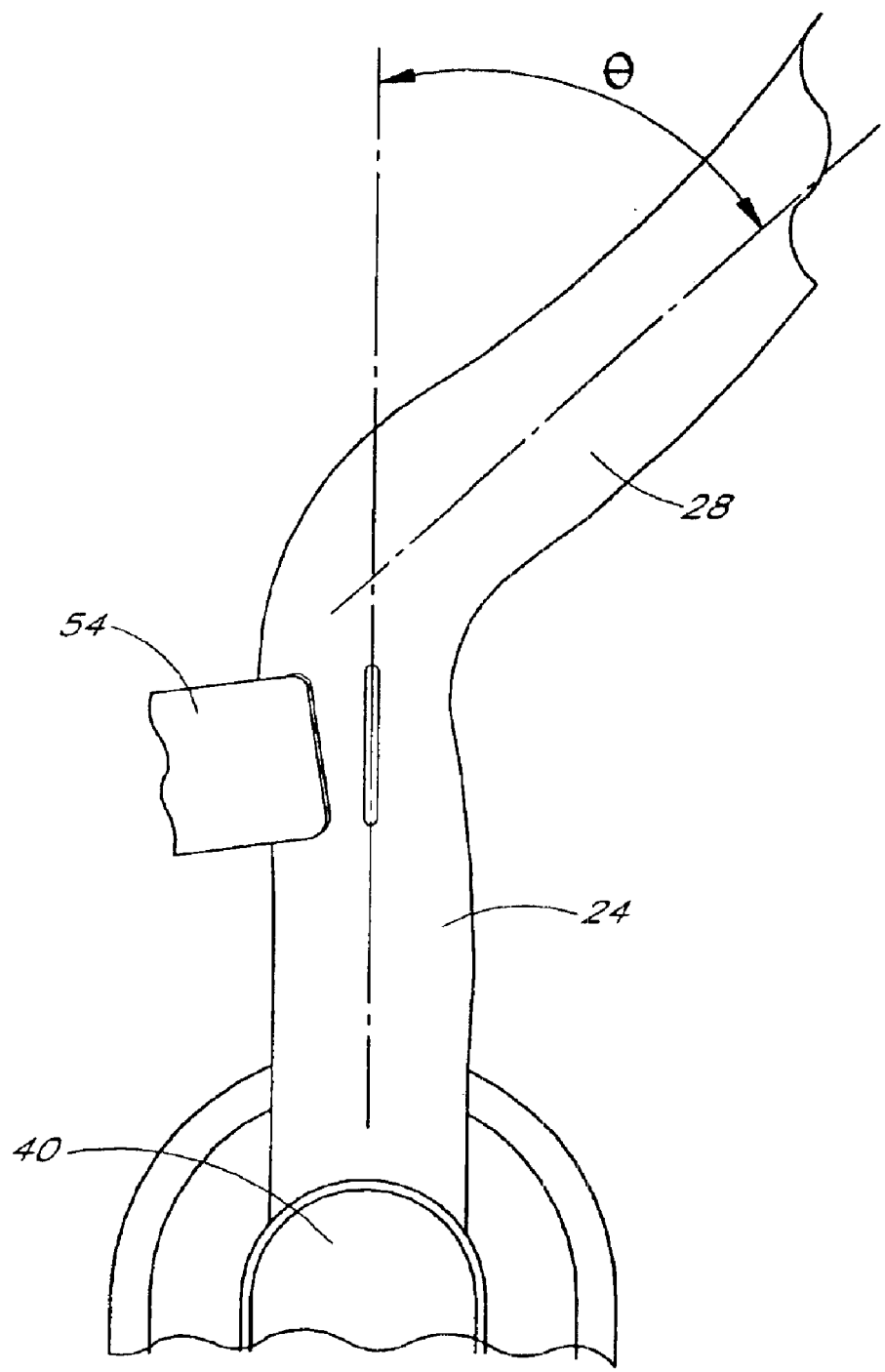
FIG. 2 is an enlarged side view showing the juncture between the upper medial segment and the angled segment of the knee brace of FIG. 1.
Figure 3:
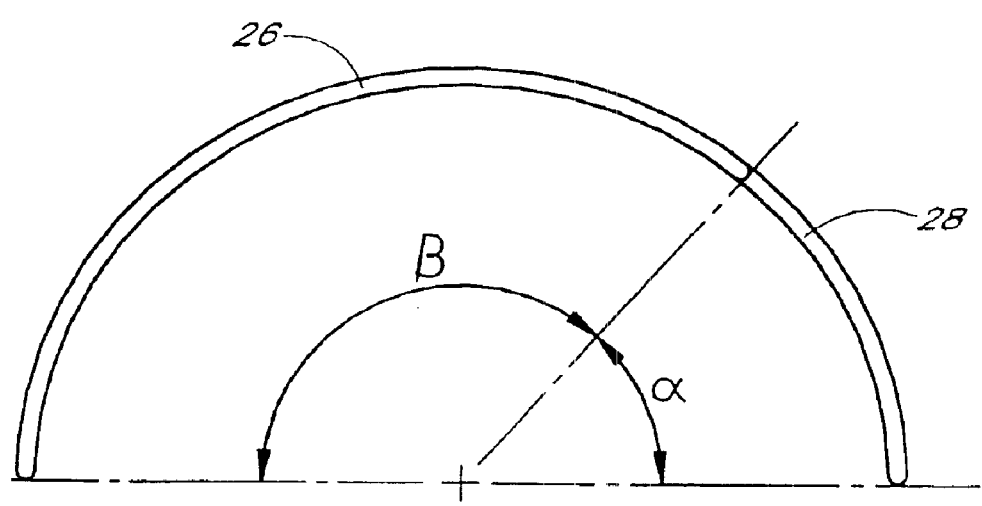
FIG. 3 is a top view of the upper curved segment of the knee brace of FIG. 1.

The angled segment 28 of the upper rigid member 20 extends upward from the top of the upper medial segment 24. As illustrated in FIG. 2, the centerlines of the upper medial segment 24 and the angled segment 28 intersect to form an angle θ. Preferably, the angle θ is between about 30 degrees and 60 degrees. Most preferably, the angle θ is about 45 degrees. In order to conform to the shape of the thigh, the angled segment 28 extends both upward from the top of the upper medial segment 24 and laterally around the leg toward the front of the thigh. As a result, the angled segment 28 provides a rigid structure that circumvents the medial superior region of the thigh. As illustrated in the embodiment of FIG. 3, the angled segment 28 extends around the left leg from the medial thigh toward the front of the thigh by an angle α. Preferably, the angle α is between about 40 degrees and 80 degrees.

The curved segment 26 at the upper end of the knee brace 10 extends horizontally around the front of the thigh to provide support. The curved segment 26 connects the top of the lateral segment 22 with the top of the angled segment 28. Still referring to FIG. 3, the curved segment 26 extends from the lateral segment towards the medial segment 28 by an angle β. Preferably, the angle β is between about 100 degrees and 140 degrees.

Referring again to FIG. 1, the knee brace 10 further comprises a first strap 52 and a second strap 54 for securing the upper rigid member 20 to the thigh. Each of the straps 52, 54 is connected to the rigid upper member 20 at two locations and extends around the back of the thigh. The straps 52, 54 are preferably thin, flexible bands that are secured with Velcro®. In a preferred embodiment, the first strap 52 is coupled to the rigid upper member 20 at the medial and lateral ends of the curved segment 26. As a result, the first strap 52 extends along a path that lies in substantially the same plane as the curved segment 26 of the rigid upper member 20. Therefore, the curved segment 26 and the first strap 52 form a circular support member around the upper thigh that provides an attachment point for the knee brace 10 and helps ensure that the knee brace is firmly secured onto the leg. The illustrated embodiment also comprises two lower straps for securing the lower rigid member 30 to the calf. Although an embodiment of the present invention is illustrated in the figures as having four straps, any number of straps may be used wherein the knee brace can be firmly secured to the leg.

In another significant feature of the present invention, the contoured shape of the rigid upper member 20 of the present invention advantageously allows for the use of rotatable strap tab caps 44 at both the medial and lateral ends of the upper curved segment 26. The rotatable strap tab caps 44 allow the upper strap 52 to be adjusted to more precisely fit the shape of the user's leg, thereby improving the comfort and effectiveness of the knee brace. As best illustrated in FIG. 1, the first strap 52 passes through strap tabs 42 which, in turn, are attached to the ends of the curved segment 26 via the rotatable strap tab caps 44 located along the exterior portion of the curved segment 26. Because the curved segment 26 of the present invention does not extend into the medial superior thigh region, the rotatable strap tab cap located on the medial end of the curved segment 26 does not cause discomfort nor interfere with the opposing leg. By contrast, it would not be desirable to mount a rotatable strap tab cap on the medial end of the upper curved portion of a prior art knee brace because the rotatable strap tab cap would be located along the medial superior portion of the thigh. As a result, the strap tab cap would cause discomfort to the user and would interfere with the natural motion of the legs.

The other straps may be connected to the upper lateral member 22 and lower lateral member 32 of the knee brace 10 using the same rotatable strap tab caps just described. Further details regarding a preferred embodiment of a rotatable strap tab cap are disclosed in Applicant's copending applications entitled: "Strap Tab Cap for a Knee Brace", application Ser. No. 09/945,120, now U.S. Pat. No. 6,425,166, filed Aug. 31, 2001, the entirety of which is hereby incorporated by reference.

Figure 4:
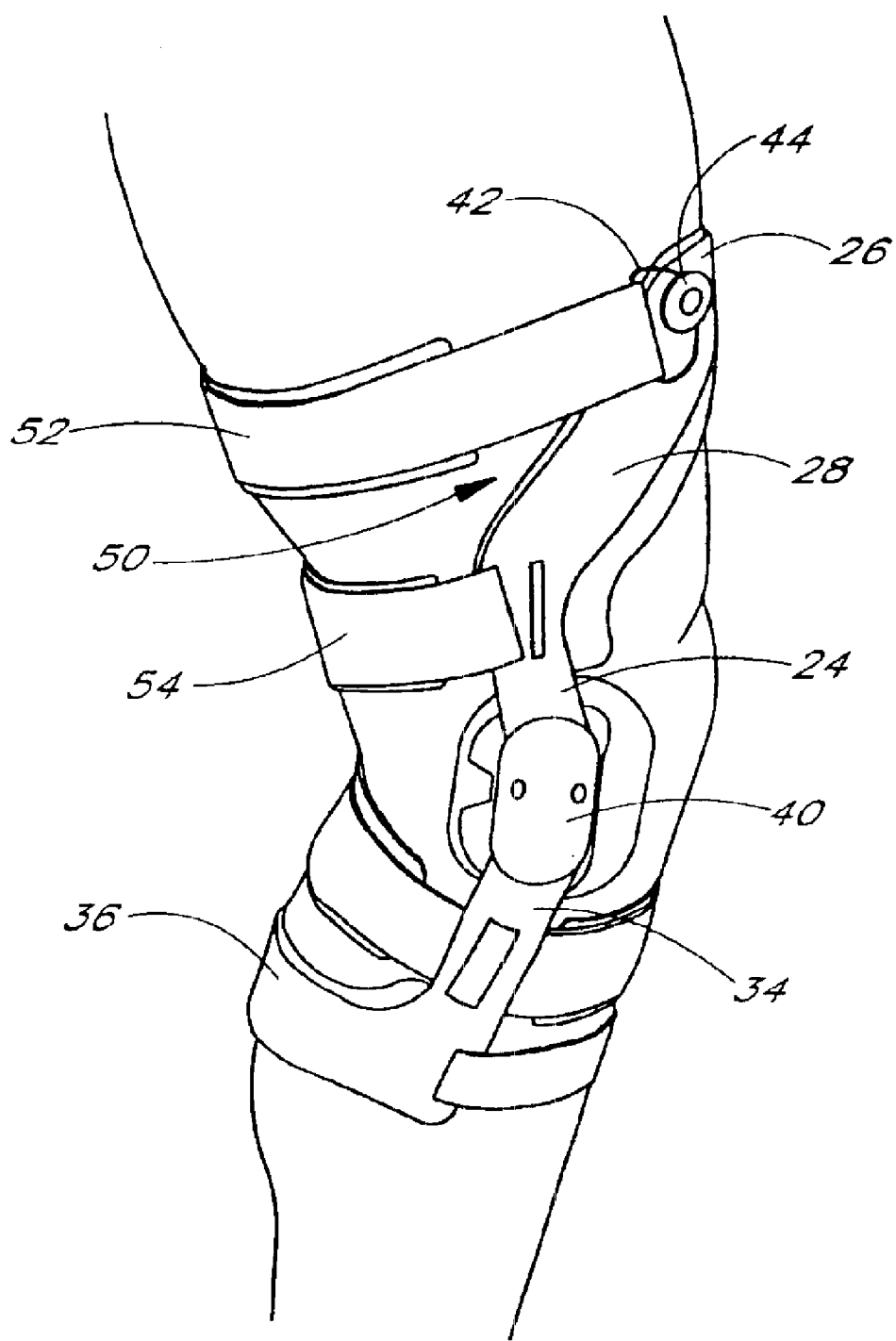
FIG. 4 is a side view of the knee brace of FIG. 1 during use.

FIG. 4 illustrates a preferred embodiment of the knee brace 10 of the present invention as used on a left leg. As seen in the illustrated embodiment, the upper rigid member 20 of the knee brace 10 is advantageously configured without any rigid structure in the region 50 along the medial superior thigh. Therefore, there is no rigid structure to produce discomfort or impede the natural motion of the leg. Furthermore, the knee brace of the present invention is configured to conform to the natural shape of the leg. Therefore, it has a ver low profile and can be worn during virtually any physical activity. Also, due to the low profile, the knee brace can be comfortably worn under long pants if desired. The snug fit provides a large number of support points that prevent the knee joint from bending in undesirable directions and therefore provides excellent stability.

The improved knee brace of the present invention is particularly advantageous for use by skiers. During skiing, the skis are preferably kept close together in a substantially parallel arrangement to provide for optimal speed and control. To achieve this configuration, the legs must be maintained close together and therefore the inner thighs frequently contact or rub against each other. Because the rigid upper member of the knee brace of the present invention does not extend into the medial superior thigh, a skier wearing the knee brace can move comfortably and is not impeded by the rigid structure of the knee brace. The ability to move comfortably and naturally is critical to a skier's performance, particularly when the skier is participating in racing or other competition. Furthermore, when the knee brace of the present invention is worn on both legs during skiing, there is no annoying clatter caused by contact between the opposing knee braces.

The improved knee brace of the present invention is also advantageous for use while riding motorcycles, and particularly while moto-cross racing. During moto-cross racing, a rider will commonly press his or her medial superior thigh against the gas tank to provide balance while making a turn and to help control the motorcycle. In the past, this maneuver has been very difficult and uncomfortable for riders wearing a knee brace because the rigid upper frame prevented close contact between the thigh and the motorcycle. However, the improved knee brace of the present invention eliminates this problem by removing the interfering structure and allows the rider to maneuver without constraint.

The upper and lower members of the knee brace are preferably made of a durable plastic, such as polypropylene, or any other durable material, such as aluminum alloy 6061 T6.

The above presents a description of the best mode contemplated for a contoured knee brace frame according to the present invention, and of the manner and process of making and using it, in such full, clear, concise, and exact terms as to enable any person skilled in the art to which it pertains to make and use this device. The embodiments of the contoured knee brace frame described herein are, however, susceptible to modifications and alternate constructions which are fully equivalent. Consequently, it is not the intention to limit this contoured knee brace frame to the particular embodiments disclosed. On the contrary, the intention is to cover all modifications and alternate constructions coming within the spirit and scope of the invention as generally expressed by the following claims, which particularly point out and distinctly claim the subject matter of the present invention.

What is claimed is:

1. A knee brace for supporting a knee joint, said knee brace having a substantially rigid upper member for attachment to a thigh, a substantially rigid lower member for attachment to a calf, and first and second hinges located about an axis of said knee joint for connecting said upper and lower members together, said upper member comprising:

a substantially straight upper lateral segment having a top end and a bottom end, said upper lateral segment extending vertically along a lateral portion of the thigh, said bottom end of said upper lateral segment being coupled to said first hinge;

a substantially straight upper medial segment having a top end and a bottom end, said upper medial segment extending vertically along a medial portion of the thigh, said bottom end of said upper medial segment being coupled to said second hinge, said upper medial segment being shorter in length than said upper lateral segment;

an upper curved segment extending horizontally around a front portion of the thigh, said upper curved segment having a lateral end and a medial end, said lateral end being joined to said top end of said upper lateral segment; and an angled segment having an upper end joined to said medial end of said upper curved segment, said angled segment having a lower end joined to said upper end of said upper medial segment, said angled segment being configured for circumventing a medial superior region of the thigh; said lower member comprising:

a substantially straight lower lateral segment having a top end and a bottom end, said lower lateral segment extending vertically along a lateral portion of the calf, said top end of said lower lateral segment being coupled to said first hinge;

a substantially straight lower medial segment having a top end and a bottom end, said lower medial segment extending vertically along a medial portion of the calf, said top end of said lower medial segment being coupled to said second hinge; and a lower curved segment extending around the calf from said bottom end of said lower lateral segment to said bottom end of said lower medial segment.

2. The knee brace of claim 1, wherein said first and second hinges are polycentric hinges.

3. The knee brace of claim 1, wherein said upper and lower members are each formed as a continuous rigid unit.

4. The knee brace of claim 1, wherein said angled segment and said upper medial segment intersect at an angle between about 30 degrees and 60 degrees.

5. The knee brace of claim 1, wherein said angled segment extends around the front portion of the thigh by about 40 degrees to 80 degrees.

6. The knee brace of claim 1, further comprising first and second straps for securing said upper member to the thigh, said first strap being substantially aligned with said upper curved segment.

7. The knee brace of claim 6, further comprising third and fourth straps, said fourth strap being substantially aligned with said lower curved segment.

8. The knee brace of claim 1, wherein no structure is provided along the thigh in the region below the upper curved segment and the angled segment.

9. The knee brace of claim 1, wherein said upper and lower members are each made of a durable plastic.

10. A knee brace for supporting a knee joint, said knee brace having a substantially rigid upper member for attachment to a thigh, a substantially rigid lower member for attachment to a calf, first and second hinges located about an axis of said knee joint for connecting said upper and lower members together, and at least a first strap for securing said upper member to the thigh, said upper member comprising:

a substantially straight upper lateral segment having a top end and a bottom end, said upper lateral segment extending vertically along a lateral portion of the thigh, said bottom end of said upper lateral segment being coupled to said first hinge;

a substantially straight upper medial segment having a top end and a bottom end, said upper medial segment extending vertically along a medial portion of the thigh, said bottom end of said upper medial segment being coupled to said second hinge, said upper medial segment being shorter in length than said upper lateral segment;

an upper curved segment extending horizontally around a front portion of the thigh, said upper curved segment having a lateral end and a medial end, said lateral end being joined to said top end of said upper lateral segment; and an angled segment having an upper end joined to said medial end of said upper curved segment, said angled segment having a lower end joined to said upper end of said upper medial segment, said angled segment being configured for circumventing a medial superior region of the thigh;

wherein said first strap is substantially aligned with said upper curved segment.

11. A knee brace for supporting a knee joint, said knee brace having a substantially rigid upper member for attachment to a thigh, a substantially rigid lower member for attachment to a calf, and first and second hinges located about an axis of said knee joint for connecting said upper and lower members together, said upper member comprising:

a substantially straight upper lateral segment having a top end and a bottom end, said upper lateral segment extending vertically along a lateral portion of the thigh, said bottom end of said upper lateral segment being coupled to said first hinge;

a substantially straight upper medial segment having a top end and a bottom end, said upper medial segment extending vertically along a medial portion of the thigh, said bottom end of said upper medial segment being coupled to said second hinge, said upper medial segment being shorter in length than said upper lateral segment;

an upper curved segment extending horizontally around a front portion of the thigh, said upper curved segment having a lateral end and a medial end, said lateral end being joined to said top end of said upper lateral segment; and an angled segment having an upper end joined to said medial end of said upper curved segment, said angled segment having a lower end joined to said upper end of said upper medial segment, said angled segment being configured for circumventing a medial superior region of the thigh;

wherein no rigid structure is provided along the thigh in the region directly below the upper curved segment and the angled segment.

12. A knee brace for supporting a knee joint, comprising:

an upper member for attachment to a thigh, said upper member including an upper lateral segment having a top end and a bottom end, an upper medial segment having a top end and a bottom end, said upper medial segment being short in length than said upper lateral segment, a contoured segment having an upper end joined to said top end of said lateral segment and a lower end joined to said top end of said medial segment, said contoured segment extending across a front portion of the thigh and substantially circumventing a medial superior region of the thigh;

a lower member for attachment to a calf including a lower lateral segment having a top end and a bottom end, a lower medial segment having a top end and a bottom end, and a lower curved segment extending around a back portion of the calf, said lower curved segment being joined to said bottom end of said lower lateral segment and said bottom end of said lower medial segment;

a first hinge for rotatably coupling said upper lateral segment to said lower lateral segment; and a second hinge for rotatably coupling said upper medial segment to said lower medial segment.

* * * * *